US008778332B2

(12) United States Patent
Toi et al.

(10) Patent No.: US 8,778,332 B2
(45) Date of Patent: Jul. 15, 2014

(54) AGENT FOR REDUCING RISK OF DEVELOPING CANCER

(75) Inventors: Masakazu Toi, Kyoto (JP); Yasuo Ohashi, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 13/500,222

(22) PCT Filed: Oct. 21, 2010

(86) PCT No.: PCT/JP2010/068545
§ 371 (c)(1),
(2), (4) Date: Apr. 4, 2012

(87) PCT Pub. No.: WO2011/049154
PCT Pub. Date: Apr. 28, 2011

(65) Prior Publication Data
US 2012/0201797 A1    Aug. 9, 2012

(30) Foreign Application Priority Data
Oct. 22, 2009 (JP) ................................. 2009-243251

(51) Int. Cl.
*A01N 63/00* (2006.01)

(52) U.S. Cl.
USPC ...................................................... 424/93.45

(58) Field of Classification Search
None
See application file for complete search history.

(56) References Cited

U.S. PATENT DOCUMENTS

| 6,572,854 B1 | 6/2003 | De Simone |
| 2003/0215429 A1 | 11/2003 | De Simone |

FOREIGN PATENT DOCUMENTS

| CN | 1265037 A | 8/2000 |
| CN | 1284994 | 2/2001 |
| CN | 1475227 | 2/2004 |
| JP | H4-235920 A | 8/1992 |
| JP | 6 96538 | 11/1994 |
| JP | 9 238647 | 9/1997 |
| JP | 3014148 | 2/2000 |
| JP | 2002 504324 | 2/2002 |
| WO | WO 99/06057 A1 | 2/1999 |
| WO | WO 99/42568 A1 | 8/1999 |

OTHER PUBLICATIONS

Hirayama et al. The role of probiotic bacteria in cancer prevention, Microbes and Infection, vol. 2, Issue 6, May 2000, pp. 681-686.*
Aryana et al., Quality attributes of yogurt with *Lactobacillus casei* and various prebiotics, LWT 40 (2007) 1808-1814.*
Nagao et al., Effects of a Fermented Milk Drink Containing *Lactobacillus casei* Strain Shirota on the Immune System in Healthy Human Subjects, Biosci. Biotechnol. Biochem., 64 (12) 2706-2708, 2000.*
Combined Office Action and Search Report issued Dec. 7, 2012 in Chinese Patent Application No. 201080045207.0 with partial English language translation and English translation of categories of cited documents.
Pieter van't Veer, et al. "Consumption of Fermented Milk Products and Breast Cancer: A Case-Control Study in the Netherlands", Cancer research, vol. 49, Jul. 15, 1989, pp. 4020-4023.
S.S. Choi, et al. "Effects of *Lactobacillus* strains on cancer cell proliferation and oxidative stress in vitro", Letters in Applied Microbiology, vol. 42, Dec. 31, 2006, pp. 452-458.
Kim, J.E., et al., "Cancer Chemopreventive Effects of Lactic Acid Bacteria," Journal of Microbiology and Biotechnology, vol. 17, No. 8, pp. 1227-1235, (2007).
Matsuoka, Y., "Probiotics no Meneki Chosetsu Kinou to Hatsugan Yobou heno Kanousei," Journal of Intestinal Microbiology, vol. 16, pp. 30-31, (2002) (with English translation).
Hayakawa, H., "Chonai Saikin ni yoru Hakko Sanbutsu no Eiyouseirikinou," Experimental Herbivora, vol. 27, pp. 1-3, (Oct. 30, 2003) (with English translation).
Ohta, T., et al., "Inhibitory effects of Bifidobacterium-fermented soy milk on 2-amino-1-methyl-6-phenylimidazo[4,5-b]pyridine-induced rat mammary carcinogenesis, with a partial contribution of its component isoflavones," Carcinogenesis, vol. 21, No. 5, pp. 937-941, (2000).
Setchell, K.D.R., "Naturally Occuring Non-Steroidal Estrogens of Dietary Origin," Estrogens in the Environment II, pp. 69-85, (1985).
Zwiller, J., et al., "Inhibition of PDGF-induced c-jun and c-fos expression by a tyrosine protein kinase inhibitor," Oncogene, vol. 6, pp. 219-221, (1991).
Sharma, O.P., et al., "Soy of Dietary Source Plays a Preventive Role Against the Pathogenesis of Prostatitis in Rats," Journal of Steroid Biochemistry and Molecular Biology, vol. 43, No. 6, pp. 557-564, (1992).
International Search Report Issued Jan. 25, 2011 in PCT/JP10/68545 Filed Oct. 21, 2010.
Office Action issued on Nov. 8, 2013 in the corresponding Chinese Patent Application No. 201080045207.0 w/partial English translation.
Extended European Search Report issued Jul. 24, 2013 in Patent Application No. 10825003.6.
Yasuo Ohashi et al., "Habitual Intake of Lactic Acid Bacteria and Risk Reduction of Bladder Cancer", Urologia Internationalis, vol. 68, No. 4, XP-009009234, May 1, 2002, pp. 273-280.
Howard Amital et al., "Probiotic Supplementation with *Lactobacillus casei* (Actimel) Induces a Th1 Response in an Animal Model of Antiphospholipid Syndrome", Annals of the New York Academy of Sciences, vol. 1110, No. 1, XP-055070467, Sep. 1, 2007, pp. 661-669.
Michael S. Donaldson et al., "Nutrition and Cancer: A Review of the Evidence for an Anti-cancer Diet", Nutrition Journal, vol. 3, No. 1, XP-021007633, Oct. 20, 2004, 21 pages.
Anna Biffi et al., "Antiproliferative Effect of Fermented Milk on the Growth of a Human Breast Cancer Cell Line", Nutrition and Cancer, vol. 28, No. 1, XP-008003102, Jan. 1, 1997, pp. 93-99.

* cited by examiner

*Primary Examiner* — Suzanne M Noakes
*Assistant Examiner* — Stephen Chong
(74) *Attorney, Agent, or Firm* — Oblon, Spivak, McClelland, Maier & Neustadt, L.L.P.

(57) ABSTRACT

Provided is an agent or a food or drink for reducing the risk of developing breast cancer. An agent for reducing the risk of developing breast cancer which comprises a composition containing living cells of *Lactobacillus casei*.

8 Claims, 2 Drawing Sheets

AGENT FOR REDUCING RISK OF DEVELOPING CANCER

This application is a National Stage of PCT/JP10/068,545 filed Oct. 21, 2010 and claims the benefit of JP 2009-243251 filed Oct. 22, 2009.

TECHNICAL FIELD

The present invention relates to an agent and a food product capable of reducing the risk of developing breast cancer by continuous ingestion thereof.

BACKGROUND ART

Breast cancer is a cancer which develops in breast tissues, and a therapeutic means for healing breast cancer is, in principle, surgery. In addition, chemotherapy or radiotherapy is used in combination with such surgery. In recent years, the number of incidences of breast cancer has rapidly increased, and breast cancer has occupied first place in morbidity among female cancers in Japan.

The highest risk factor of developing breast cancer is family history. In addition, it is considered that a long-term state of estrogen excess is reflected in the development of breast cancer. Specifically, there have been known risk factors such as no pregnancy history/parity, no experience of breast feeding after the birth of the first child, an early age at menarche, a late age at menopause, and experience of hormone therapy.

It has been reported that soy isoflavones have female hormone-like action and inhibitory action on carcinogenesis (Non Patent Documents 1-3 and Patent Document 1). On the other hand, it has been known that a group of lactic acid bacteria of the genus *Streptococcus*, the genus *Bifidobacterium*, the genus *Lactobacillus*, and the like have inhibitory action on recurrence of bladder cancer, arginine deiminase activity, and the like (Patent Documents 2 and 3). Moreover, it has also been known that dead cells of microorganisms of the genus *Lactobacillus* have anticarcinogenic action (Patent Document 4).

PRIOR ART DOCUMENTS

Patent Document

[Patent Document 1] JP-A-9-238647
[Patent Document 2] JP-B-3014148
[Patent Document 3] JP-A-2002-504324
[Patent Document 4] JP-B-6-96538

Non Patent Document

[Non Patent Document 1] K. D. R. Setchell, In Estrogens in the Environment, ed by J. A. Mclachlen, pp. 69-85 [[60-85]], Elsevier Science Publishing Co., Inc., New York, 1985
[Non Patent Document 2] Oncogene, 6, 219, 1991
[Non Patent Document 3] J. Steroid Biochem. Mol. Biol, 43, 557, 1992

SUMMARY OF THE INVENTION

Problems to be Solved by the Invention

An object of the present invention is not to treat the developed breast cancer, but to provide an agent or a food or drink for reducing the risk of developing breast cancer by ingestion thereof before the development of breast cancer.

Means for Solving the Problems

Thus, the present inventors have studied the relationship between ingestion of lactic acid bacteria and the risk of developing breast cancer. As a result, the inventors have found that the incidence of breast cancer in women who ingested a composition containing living cells of *Lactobacillus casei* is statistically significantly lower than the incidence of breast cancer in women who did not ingest such a composition. In addition, the inventors have also found that the incidence of breast cancer in women who ingested both *Lactobacillus casei* and a soybean-derived ingredient is further decreased, thereby completing the present invention.

Accordingly, the present invention provides an agent for reducing the risk of developing breast cancer, including a composition containing living cells of *Lactobacillus casei*.

The present invention also provides an agent for reducing the risk of developing breast cancer, including a composition containing living cells of *Lactobacillus casei* and a soybean-derived ingredient.

The present invention also provides a method for reducing the risk of developing breast cancer, including ingesting a composition containing living cells of *Lactobacillus casei* or a composition containing living cells of *Lactobacillus casei* and a soybean-derived ingredient before the development of breast cancer.

The present invention also provides a composition containing living cells of *Lactobacillus casei*, or a composition containing living cells of *Lactobacillus casei* and a soybean-derived ingredient, for use in reducing the risk of developing breast cancer.

The present invention also provides use of a composition containing living cells of *Lactobacillus casei* or a composition containing living cells of *Lactobacillus casei* and a soybean-derived ingredient for production of an agent for reducing the risk of developing breast cancer.

Effects of the Invention

According to the present invention, the risk of developing breast cancer can be significantly reduced by ingestion of a composition containing living cells of *Lactobacillus casei*.

EMBODIMENTS FOR CARRYING OUT THE INVENTION

Figure 1:
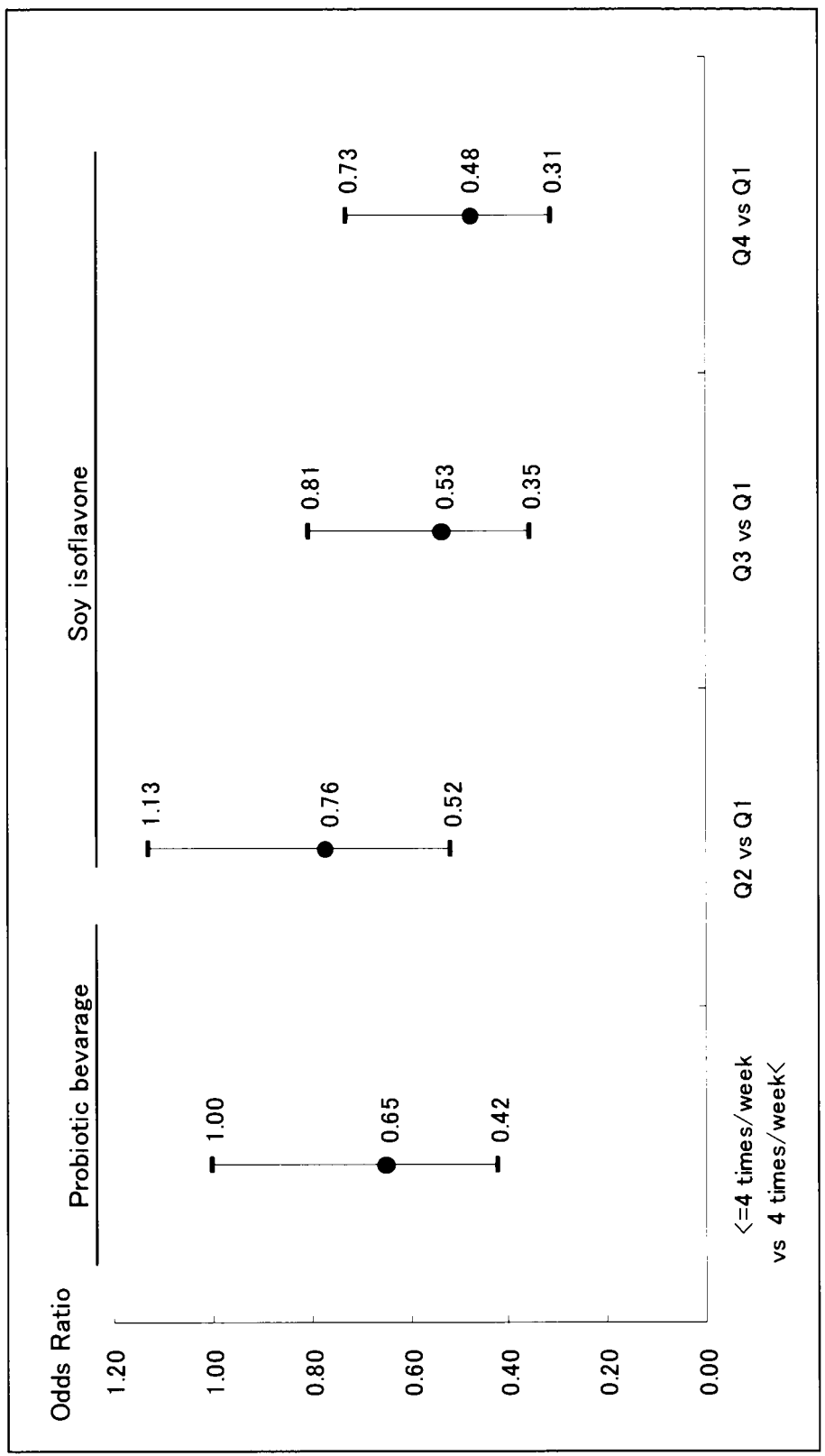
FIG. 1 is a graph showing the influence of ingestion of *casei* or a soybean-derived ingredient on the odds ratio of the development of breast cancer (wherein, in the graph, Probiotic bevarage indicates a food product containing *casei*, Soy isoflavone Q1 indicates subjects who did not ingest soybean-derived isoflavones (less than 18.76 mg/day), Q2 indicates a low ingestion group (18.76 to 28.81 mg/day), Q3 indicates a medium ingestion group (28.81 to 43.75 mg/day), and Q4 indicates a high ingestion group (43.75 or more mg/day)).

An active ingredient of the agent for reducing the risk of developing breast cancer of the present invention consists of living cells of *Lactobacillus casei*, or a combination of living cells of *Lactobacillus casei* with a soybean-derived ingredient.

The utility form of *Lactobacillus casei* in the composition used in the present invention is not particularly limited. *Lactobacillus casei* may be freeze-dried or spray-dried, or it may also be used in the form of a culture product or processed product containing the cells thereof. *Lactobacillus casei* may have any form, as long as cells can be present alive. The strain of *Lactobacillus casei* is not particularly limited. Preferred examples of the strain of *Lactobacillus casei* include *Lactobacillus casei* YIT 9018 (FERM BP-665), *Lactobacillus casei* YIT 9029 (FERM BP-1366), and *Lactobacillus casei* YIT 10003 (FERM BP-7707). Of these, *Lactobacillus casei* YIT 9029 is particularly preferable.

The composition of the present invention can be used either via oral administration or via parenteral administration. Of these, oral administration is preferable. Upon administration, a composition containing living cells of *Lactobacillus casei* as an active ingredient may be mixed with a solid or liquid, nontoxic pharmaceutical carrier, which is suitable for an administration method such as oral administration, intrarectal administration or injection, and then administered in the form of a commonly used pharmaceutical preparation. Examples of such a preparation include: solid agents such as a tablet, a granule, powder and a capsule; liquid agents such as a solution, a suspension and an emulsion; and freeze-dried preparations. These preparations can be prepared according to an ordinary method for producing preparations. Examples of the aforementioned nontoxic pharmaceutical carrier include glucose, lactose, sucrose, starch, mannitol, dextrin, fatty acid glyceride, polyethylene glycol, hydroxyethyl starch, ethylene glycol, polyoxyethylene sorbitan fatty acid ester, amino acid, gelatin, albumin, water, and saline. In addition, commonly used excipients such as a stabilizer, a humectant, an emulsifying agent, a binder, a tonicity agent and a diluent can be appropriately added, as necessary.

Products which are available as pharmaceutical preparations may also be used. Pharmaceutical preparations containing living cells of *Lactobacillus casei*, which are manufactured by Yakult Honsha Co., Ltd., can be preferably used. Specific examples of such pharmaceutical preparations include "Yakult BL Seichoyaku intestinal regulator" and "Yakult BL Seichoyaku intestinal regulator S-Tablet." Also, there is "Biolactis Powder" as a pharmaceutical product for medical use.

The composition of the present invention can be used not only as a pharmaceutical preparation as described above, but also as a food or drink containing living cells of *Lactobacillus casei*. When the living cells of *Lactobacillus casei* are incorporated into a food or drink, they may be employed as is, or mixed with various nutritional ingredients. The composition of the present invention can be used as a health food or food material which is useful for reduction of the risk of developing breast cancer. An indication may be attached on such a food or drink or a container thereof so as to indicate that the product has the aforementioned effects. When living cells of *Lactobacillus casei* are specifically incorporated into a food or drink, additives which can be used for such foods and drinks are used, as appropriate, and the living cells of *Lactobacillus casei* may be processed through conventional means into a form suitable for food products, namely, a granule, a particle, a tablet, a capsule, a paste, etc. Moreover, the composition of the present invention may be added to various food products including, for example, processed meat products such as ham and sausage, processed seafood products such as kamaboko and chikuwa, bread, confectionery, butter and powdered milk. Alternatively, the composition of the present invention may also be added to beverages such as water, fruit juice, milk, soft drinks and tea drinks.

Furthermore, as foods and drinks, fermented foods and drinks containing living *Lactobacillus casei*, such as fermented milk foods and drinks, fermented soymilk, fermented fruit juice and fermented vegetable juice, are preferably used. Of these, fermented milk foods and drinks are particularly preferably used. Such fermented milk foods and drinks may be produced according to ordinary methods. For example, when fermented milk is produced, *Lactobacillus casei* is inoculated to a sterilized milk medium, alone or simultaneously with other microorganisms, and it is then cultured. Thereafter, the obtained culture is subjected to a homogenization treatment to obtain a fermented milk base. Subsequently, a syrup solution which has been prepared, separately, is added to and mixed with the fermented milk base, and the obtained mixture is then homogenized with a homogenizer or the like. Thereafter, a flavor is further added to the resultant, so as to obtain a final product. The thus obtained fermented milk food or drink may have any form, namely, a plain type containing no syrup (sweetener), a soft type, a fruit-flavored type, a solid, a liquid, etc.

Such a fermented milk food or drink may contain any given ingredients including sweeteners such as syrup, emulsifiers, thickeners (stabilizers), and various types of vitamins. Examples of the syrup include: sugars such as glucose, sucrose, fructose, high-fructose corn syrup, glucose fructose syrup, palatinose, trehalose, lactose, xylose, maltose, honey and molasses; sugar alcohols such as sorbitol, xylitol, erythritol, lactitol, Palatinit, reduced sugar syrup and reduced malt sugar syrup; and high intensity sweeteners such as aspartame, thaumatin, sucralose, acesulfame K and stevia. Moreover, such a fermented milk food or drink may also contain: emulsifiers such as sucrose fatty acid ester, glycerin fatty acid ester, polyglycerin fatty acid ester, sorbitan fatty acid ester and lecithin; and thickeners (stabilizers) such as agar, gelatin, carrageenan, guar gum, xanthan gum, pectin, locust bean gum, gellan gum, carboxymethyl cellulose, soybean polysaccharides and propylene glycol alginate. Other than these substances, such a fermented milk food or drink may further contain: vitamins such as vitamin A, vitamin Bs, vitamin C and vitamin Es; minerals such as calcium, magnesium, zinc, iron and manganese; acidulants such as citric acid, lactic acid, acetic acid, malic acid, tartaric acid and gluconic acid; milk fats such as cream, butter and sour cream; flavors such as flavors from yogurt, berry, orange, quince, perilla, citrus, apple, mint, grape, apricot, pear, custard cream, peach, melon, banana, tropical fruits, herb, tea, coffee, etc.; herb extracts; and brown sugar extracts.

Microorganisms other than *Lactobacillus casei* can be used in combination with *Lactobacillus casei* for production of fermented milk foods and drinks. Examples of such microorganisms include: bacteria of the genus *Bifidobacterium*, such as *Bifidobacterium breve, B. longum, B. bifidum, B. animalis, B. suis, B. infantis, B. adolescentis, B. catenulatum, B. pseudocatenulatum, B. lactis*, and *B. globosum*; bacteria of the genus *Lactobacillus*, such as *L. acidophilus, L. plantarum, L. buchneri, L. gallinarum, L. amylovorus, L. brevis, L. rhamnosus, L. kefir, L. paracasei, L. crispatus, L. zeae, L. helveticus, L. salivalius, L. gasseri, L. fermentum, L. reuteri, L. crispatus, L. delbrueckii subsp. bulgaricus, L. delbrueckii* subsp. *delbrueckii*, and *L. johnsonii*; bacteria of the genus *Streptococcus*, such as *Streptococcus thermophilus*; bacteria of the genus *Lactococcus*, such as *Lactococcus lactis* subsp. *lactis* and *Lactococcus lactis* subsp. *cremoris*; bacteria of the genus *Enterococcus*, such as *Enterococcus faecalis* and *E. faecium*; bacteria of the genus *Bacillus*, such as *Bacillus subtilis*; and yeasts belonging to the genus *Saccharomyces*, the genus *Torulaspora* and the genus *Candida*, such as *Saccharomyces cerevisiae, Torulaspora delbrueckii*, and *Candida kefyr*. Such fermented milk foods and drinks are preferably produced by a combined use of *Lactobacillus casei* with one or more types selected from the group consisting of bacteria of the genus *Lactobacillus* other than *Lactobacillus casei*, bacteria of the genus *Streptococcus*, and bacteria of the genus *Lactococcus*, because high palatability can be obtained and it becomes easy to ingest the thus produced fermented milk foods and drinks.

Furthermore, commercially available products may also be used as such fermented milk foods and drinks. Fermented milk foods and drinks containing living cells of *Lactobacillus casei*, which are manufactured by Yakult Honsha Co., Ltd., can be preferably used. Specific examples of such products include Yakult products such as "Yakult," "Yakult 300V," "Yakult SHEs" and "Yakult 400," and other products such as "Joie," "Sofuhl," "Purela" and "Pretio." Of these, Yakult products are particularly preferably used because they contain a large number of living cells of *Lactobacillus casei*.

The composition of the present invention containing living cells of *Lactobacillus casei* used as an active ingredient has conventionally been used as a food product, and its safety has been confirmed. Accordingly, when the composition of the present invention is used, the intake thereof is not strictly limited. The intake thereof is preferably $10^5$ cfu to $10^{13}$ cfu of, and particularly preferably $10^8$ cfu to $10^{12}$ cfu of living cells of *Lactobacillus casei* per day. From the viewpoint of effective reduction of the risk of developing breast cancer, the frequency of ingesting the composition is preferably high, and particularly preferably 4 or more times per week. In addition, the period in which the composition is ingested is preferably long, and particularly preferably, the composition is continuously ingested for 10 or more years. Moreover, with regard to the age of a subject who ingests the composition, a subject, approximately 20 years old, who would be at 20 to 35 years before the development of breast cancer, preferably ingests the composition 4 or more times per week.

The composition of the present invention may contain a soybean-derived ingredient. By ingesting such a soybean-derived ingredient together with living cells of *Lactobacillus casei*, the risk of developing breast cancer can be more effectively reduced. Such a soybean-derived ingredient can be used in the form of a soybean itself or a soybean-processed product. Examples of the soybean-processed product include miso, tofu, koya-tofu, shimi-dofu, nama-age, atsu-age, abura-age, natto, soymilk, soy sauce, tempeh and supplements and health food products which contains a soybean-derived ingredient such as isoflavones.

The timing when the soybean-derived ingredient is ingested is not particularly limited. It may be ingested simultaneously with *Lactobacillus casei*, or it may be ingested before or after ingestion of *Lactobacillus casei*. A preferred example of the soybean-derived ingredient, which is ingested simultaneously with *Lactobacillus casei*, is fermented soymilk containing living cells of *Lactobacillus casei*. The intake of the soybean-derived ingredient is 18.76 mg or more, preferably 28.81 mg or more, and more preferably 43.75 mg or more, per day, as described in the following Examples.

If the composition of the present invention is ingested before the development of breast cancer, the risk of developing breast cancer can be reduced, and thus, the development of breast cancer can be prevented. Moreover, even after the development of breast cancer, the risk of recurrence of breast cancer can be reduced by ingesting the composition of the present invention after the breast cancer is excised, diminished or vanished by surgery, administration of drugs, radiotherapy, etc.

EXAMPLES

Next, the present invention will be described in more detail by way of Examples. However, these Examples are not intended to limit the scope of the present invention.

Examples

In terms of habitual ingestion of a composition containing *Lactobacillus casei*, patients with breast cancer and subjects without breast cancer were examined using self-administered questionnaires and according to interview techniques. In addition, in terms of ingestion of soy isoflavones as well, they were examined by the same methods as described above.

1. Subjects

Cases: 306 cases, female patients with breast cancer from 40 to 55 years old (within 1 year after surgery)

Controls: 662 controls, subjects without breast cancer, whose sex, age and area of residence were matched with those of the aforementioned cases. (It is to be noted that 1 control case was eliminated from the analysis because of deficiency of an adjustment factor.)

The background of the subjects is shown in Table 1. The data in the table are each indicated with n (number) (%) or a mean value (standard deviation).

TABLE 1

|  | Case (n = 306) | Control (n = 662) |
|---|---|---|
| Age | 47.5 (4.1) | 47.3 (3.7) |
| 40's | 199 (65.0%) | 461 (69.6%) |
| 50's | 107 (35.0%) | 201 (30.4%) |
| Educational background |  |  |
| Other than university or graduate school | 264 (86.3%) | 518 (78.3%) |
| University, graduate school, or higher education | 42 (13.7%) | 144 (21.8%) |
| Physical activity level (Mets/day) | 26 (13.3) | 27 (12.8) |
| Anamnesis of benign mammary tumor | 51 (16.7%) | 41 (6.2%) |
| Family breast cancer history | 29 (9.5%) | 28 (4.2%) |
| Age at menarche (years) | 13 (1.3) | 13 (1.3) |
| Number of births | 2 (1.0) | 2 (1.1) |
| Breast feeding history | 232 (75.8%) | 528 (79.8%) |
| Menopause | 111 (36.3%) | 200 (30.2%) |
| History of use of female hormone agent |  |  |
| Not used | 254 (83.0%) | 553 (83.5%) |
| During use/previously used | 52 (17.0%) | 109 (16.5%) |
| Body weight at birth |  |  |
| ≥2500 g | 270 (88.2%) | 584 (88.2%) |
| <2500 g | 21 (6.8%) | 48 (7.3%) |
| Unknown/data not available | 15 (4.9%) | 30 (4.5%) |
| BMI (kg/m$^2$) at age 20 years | 20 (2.4) | 20 (2.2) |
| Smoking | 38 (12.4%) | 78 (11.8%) |
| Energy intake (1000 kcal/day) | 2 (0.8) | 2 (0.8) |

2. Composition Containing *Lactobacillus casei*

"Yakult" (manufactured by Yakult Honsha Co., Ltd.)

"Yogurt products containing *Lactobacillus casei*, such as Joie and Sofuhl"

The aforementioned products (Yakult, Joie and Sofuhl) all contain living cells of *Lactobacillus casei* YIT 9029.

3. Soybean-Derived Ingredient

As food products containing soy isoflavones, the following 9 food products were examined in terms of ingestion frequency and an average intake for single ingestion.

Miso soup

Tofu (boiled tofu, cold tofu)

Nama-age, atsu-age

Natto

Health food products and supplements containing soy isoflavones

Tofu (as a filling of miso soup)

Koya-tofu, shimi-dofu

Abura-age

Soymilk

4. Analysis of main evaluation items (studies regarding relationship between ingestion of *Lactobacillus casei* (hereinafter abbreviated as "casein) and the development of breast cancer)

(i) Definition of intake of *casei*

As foods and drinks (hereinafter abbreviated as "food products") containing *casei*, the above-mentioned two food products were examined in terms of ingestion frequency and an average intake for single ingestion.

A binary variable of the presence or absence of exposure to *casei* in these food products (namely, whether or not a subject has ingested *casei*) is defined for women from the upper grades of elementary school, who are assumed to have generally experienced menarche.

Specifically, a case in which a mean ingestion frequency of *casei* is less than 4 times per week is defined as "not exposed." A case in which a mean ingestion frequency of *casei* is 4 or more times per week in "the upper grades of elementary school (10 to 12 years old)," "approximately 20 years old," and "15 to 10 years ago" is defined as "exposed."

Moreover, in order to study the dose response relationship between the development of breast cancer and *casei* ingestion, 4 categories, namely, "not eat (not drink)," "1 to 3 times per month," "1 to 3 times per week," and "4 or more times per week" were also used. As a method for categorizing the aforementioned *casei* ingestion frequency, ingestion frequencies in "the upper grades of elementary school (10 to 12 years old)," "approximately 20 years old," and "15 to 10 years ago" are scored and classified as follows.

<Scoring Method>

(1) With regard to the ingestion frequency of each food product in each period, it is in principle decided that, as an ingestion frequency, *casei* is ingested once a day for 28 days (1 month) (=7 days/week×4), and the number of *casei* ingestion days is scored as follows. It is to be noted that, regarding a period questioned while providing a certain range, a period as a median thereof is adopted.

2 or more times every day=56 (=2 times/day×28 days/month)

1 time every day=28 (=1 time/day×28 days/month)

4 to 6 times per week=20 (=1 time/day×5 days/week×4 weeks/month)

2 or 3 times per week=10 (=1 time/day×2.5 days/week×4 weeks/month)

1 time per week=4 (=1 time/day×1 day/week×4 weeks/month)

2 or 3 times per month=2.5 (=1 time/day×2.5 days/month)

1 time per month=1 (=1 time/day×1 day/month)

Not drink=0

(2) A value obtained by summing all of the scores described in (1) above of individual periods and individual food products and then dividing the total score by {number of periods (three periods)×number of weeks in a month (4 weeks)}, namely, a mean ingestion frequency for a week (hereinafter referred to as a "mean score") is calculated. It is to be noted that such a mean score is rounded off to the closest whole number.

(3) The obtained mean scores are categorized into the following: "not drink," "less than 1 time per week," "1 to 3 times per week," and "4 or more times per week."

(ii) Analysis Method

First, with regard to the presence or absence of *casei* ingestion and the presence or absence of the development of breast cancer, there is calculated a 95% confidence interval, which is assumed from an odds ratio and a Wald test. For a null hypothesis test, a McNemar test is applied.

Second, there is calculated a 95% confidence interval, which is assumed from the odds ratio and the Wald test based on a conditional logistic regression analysis, in which matching factors of area of residence and age and a plurality of adjustment factors are taken into consideration. The adjustment factors used herein as continuous data include age at menarche, energy intake, momentum, the number of births, and Body Mass Index around 20 years old. On the other hand, the adjustment factors used herein as categorical data include marriage status, educational background, the experience of smoking, the experience of use of female hormone agent, the experience of suffering from mastopathy, the presence or absence of a family member who was/is suffering from breast cancer, the experience of breast feeding, and body weight at birth.

Moreover, there is calculated a 95% confidence interval, which is assumed from the odds ratio and the Wald test based on a conditional logistic regression analysis, in which only area of residence is used as a matching factor and age is used as a continuous variable and taken into consideration with a plurality of other adjustment factors.

Furthermore, there is calculated a 95% confidence interval, which is assumed from the odds ratio and the Wald test based on a conditional logistic regression analysis, in which only area of residence is used as a matching factor and age is categorized into 40's and 50's and taken into consideration with a plurality of other adjustment factors.

It is to be noted that the above described analysis is carried out in two ways, namely, an analysis in which matching is considered and an analysis in which matching is not considered. Further, an analysis is carried out even based on the experience of menopause.

5. Studies Regarding Relationship Between Length of *Casei* Ingestion Period and the Development of Breast Cancer (i) Definition of Length of *Casei* Ingestion Period The length of a *casei* ingestion period is classified into 4 categories, namely, "not ingested," "less than 5 years," "5 years or more to less than 10 years," and "10 or more years." The dose response relationship was examined in terms of the presence or absence of the development of breast cancer and the *casei* ingestion period.

(ii) Analysis Method

The same analysis method as described above is applied.

6. Studies Regarding Relationship Between Ingestion of Soy Isoflavones and the Development of Breast Cancer (i) Definition of Soy Isoflavone Intake Soy isoflavone intake is classified into 4 categories based on quartile points. The dose response relationship was examined in terms of the presence or absence of the development of breast cancer and the soy isoflavone intake.

(ii) Method of Calculating Soy Isoflavone Intake

A soy isoflavone intake is calculated using the following calculation method.

<Soy Isoflavones, Calculation Method>

Intake of Soybean Products (1) An appropriate numerical value selected from the following is placed into a category as an option of ingestion frequency of each food product.
Less than 1 time per month=0
1 to 3 times per month=2/30
1 or 2 times per week=1.5/7
3 or 4 times per week=3.5/7
5 or 6 times per week=5.5/7
1 time every day=1
2 or 3 times every day=2.5
4 to 6 times every day=5
7 or more times every day=8

(2) An appropriate numerical value selected from the following is placed into a category as an option of average intake.
Smaller than the average intake=1/2
Same as the average intake=1
Larger than the average intake=3/2

(3) Calculation of intake of soybean product

Intake (g/day) of tofu (as a filler of miso soup)=value (1)*value (2)*20

Intake (g/day) of tofu (boiled tofu, cold tofu or the like)=value (1)*value (2)*75

Intake (g/day) of koya-tofu or shimi-dofu=value (1)*value (2)*60

Intake (g/day) of nama-age or atsu-age=value (1)*value (2)*60

Intake (g/day) of abura-age=value (1)*value (2)*2

Intake (g/day) of natto=value (1)*value (2)*50

Intake of Soymilk (4) An appropriate numerical value selected from the following is placed into a category as an option of ingestion frequency of soymilk.
Less than 1 time per week=0
1 or 2 times per week=1.5/7
3 or 4 times per week=3.5/7
5 or 6 times per week=5.5/7
1 cup every day=1
2 or 3 cups every day=2.5
4 to 6 cups every day=5
7 to 9 cups every day=8
10 or more cups every day=11

(5) Calculation of intake of soymilk

Intake (g/day) of soymilk=value (4)*200

Intake of Miso Soup (6) An appropriate numerical value selected from the following is placed into a category as an option of ingestion frequency of miso soup.
Hardly ingested=0
1 to 3 times per month=2/30
1 or 2 times per week=1.5/7
3 or 4 times per week=3.5/7
5 or 6 times per week=5.5/7
Ingested every day=1

(7) An appropriate numerical value selected from the following is placed into a category as an option of intake of miso soup.
Less than 1 bowl=0.5
1 bowl=1
2 bowls=2
3 bowls=3
4 bowls=4
5 bowls=5
6 bowls=6
7 to 9 bowls=8
More than 10 bowls=11

(8) An appropriate numerical value selected from the following is placed into a category as an option of taste of miso soup.
Significantly light taste=0.5
Slightly light taste=0.75
Normal taste=1
Slightly strong taste=1.25
Significantly strong taste=1.5

(9) Calculation of intake of miso soup

Intake (g/day) of miso soup=value (6)*value (7)*value (8)*150

(10) Calculation of Isoflavone Intake

Using the values (3), (5) and (9) above, $$\text{genistein (mg/day)} = \text{intake (g/day) of tofu (as a filler of miso soup)} * (27 \text{ mg}/100 \text{ g}) + \text{intake (g/day) of tofu (boiled tofu, cold tofu or the like)} * (27/100) + \text{intake (g/day) of koya-tofu or shimi-dofu} * (9/100) + \text{intake (g/day) of nama-age or atsu-age} * (26/100) + \text{intake (g/day) of abura-age} * (18/100) + \text{intake (g/day) of natto} * (61/100) + \text{intake (g/day) of soymilk} * (16/100) + \text{intake (g/day) of miso soup} * (2/100),$$

and $$\text{daidzein (mg/day)} = \text{intake (g/day) of tofu (as a filler of miso soup)} * (17/100) + \text{intake (g/day) of tofu (boiled tofu, cold tofu or the like)} * (17/100) + \text{intake (g/day) of koya-tofu or shimi-dofu} * (3/100) + \text{intake (g/day) of nama-age or atsu-age} * (15/100) + \text{intake (g/day) of abura-age} * (8/100) + \text{intake (g/day) of natto} * (37/100) + \text{intake (g/day) of soymilk} * (8/100) + \text{intake (g/day) of miso soup} * (2/100).$$

Isoflavones (mg/day) = genistein (mg/day) + daidzein (mg/day).

(iii) Analysis Method

The same analysis method as described above is applied.

7. Studies Regarding Interaction of *Casei* with *Isoflavones*

Interaction of *casei* ingestion with soy isoflavone ingestion was also analyzed. In the analysis of such interaction, 8 combinations from 2 categories of *casei* (less than 4 times per week and 4 or more times per week) and 4 categories of soy isoflavones (quartile points) are used. Then, a group, in which *casei* is ingested less than 4 times per week and soy isoflavones are not ingested, is used as a standard category, and the odds ratio of each group is assumed. The same analysis models as those described above are used herein.

8. Studies Regarding Relationship Between Yakult Ingestion and the Development of Breast Cancer (i) Definition of Categorization of Yakult Intake Yakult intake was examined by the same method as that employed in the case of "*casei*" which is an exposure factor in main evaluation items. Accordingly, the same categorization as described above is applied to Yakult intake.

(ii) Analysis Method

The same analysis method as described above is applied.

9. Results (i) The odds ratio of the development of breast cancer in subjects who ingested food products containing *casei* 4 or more times per week was found to be 0.647 (95% confidence interval (CI): 0.420-0.997, p=0.0483), when compared with subjects who did not ingest such food products (FIG. 1). In particular, the odds ratio of the development of breast cancer in subjects who ingested food products containing *casei* 4 or more times per week when they were approximately 20 years old was found to be 0.583 (95% CI: 0.371-0.915, p=0.0190), when compared with subjects who did not ingest such food products. If analysis was carried out based on the experience of menopause, before experiencing menopause, the odds ratio of the development of breast cancer in subjects who ingested food products containing *casei* 4 or more times per week was found to be 0.779 (95% CI: 0.460-1.321, p=0.3542), when compared with subjects who did not ingest such food products. On the other hand, after experiencing menopause, the odds ratio of the development of breast cancer in subjects who ingested food products containing *casei* 4 or more times per week was found to be 0.429 (95% CI: 0.186-0.985, p=0.0461), when compared with subjects who did not ingest such food products. Moreover, the odds ratio of the development of breast cancer in subjects who have ingested food products containing *casei* for 10 or more years was found to be 0.815 (95% CI: 0.539-1.234), when compared with subjects who have not ingested such food products.

Ingestion of food products containing *casei* 4 or more times per week or for 10 or more years tended to decrease the development of breast cancer.

(ii) The odds ratio of the development of breast cancer in subjects who ingested Yakult 4 or more times per week was found to be 0.742 (95% CI: 0.397-1.389, p=0.3515), when compared with subjects who did not ingest Yakult, and thus, ingestion of Yakult tended to decrease the development of breast cancer.

(iii) With regard to ingestion of soybean (soybean products), the odds ratio of the development of breast cancer in a low ingestion group (18.76 to 28.81 mg/day) was found to be 0.763 (95% CI: 0.517-1.126), that in a medium ingestion group (28.81 to 43.75 mg/day) was found to be 0.532 (95% CI: 0.352-0.805), and that in a high ingestion group (43.75 or more mg/day) was found to be 0.476 (95% CI: 0.311-0.727), when compared with subjects who did not ingest such soybean products (less than 18.76 mg/day). Thus, ingestion of soybean products tended to decrease the development of breast cancer (linearity p=0.0002) (FIG. 1).

Reduction of the risk of developing breast cancer by ingestion of soybeans has also been reported by other studies. Such results of other studies support the accuracy of the present study, and increase the reliability of the result that habitual ingestion of food products containing *casei*, such as Yakult, reduces the risk of developing breast cancer.

Figure 2:
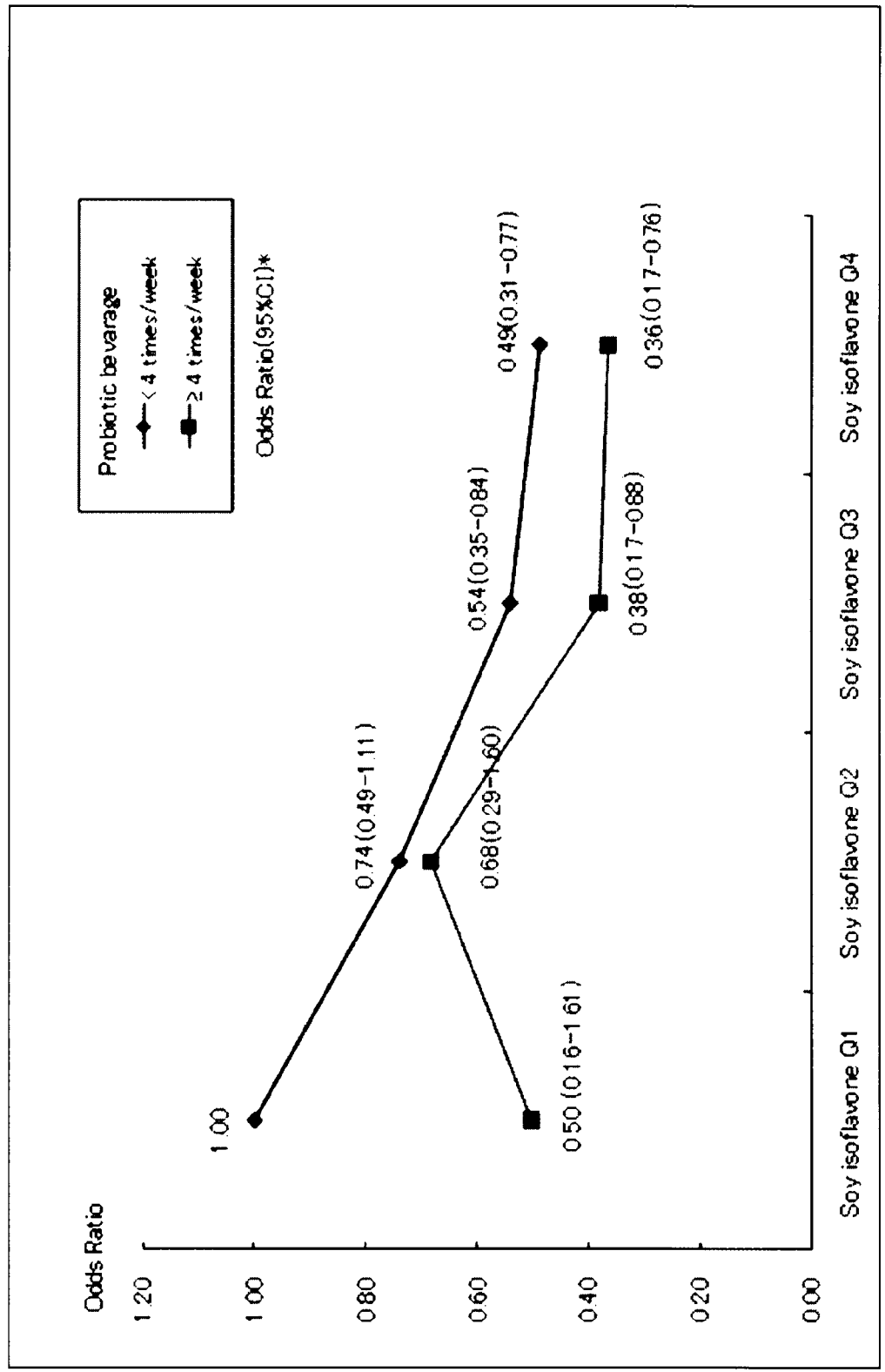
FIG. 2 is a graph showing the interaction (odds ratio) of ingestion of *casei* with ingestion of a soybean-derived ingredient (wherein, in the graph, Probiotic bevarage indicates a food product containing *casei*, Soy isoflavone Q1 indicates subjects who did not ingest soybean-derived isoflavones (less than 18.76 mg/day), Q2 indicates a low ingestion group (18.76 to 28.81 mg/day), Q3 indicates a medium ingestion group (28.81 to 43.75 mg/day), and Q4 indicates a high ingestion group (43.75 or more mg/day)).

(iv) The combination of *casei* ingestion with ingestion of a soybean-derived ingredient tended to decrease the odds ratio of the development of breast cancer, when food products containing *casei* were ingested 4 or more times per week. In particular, such a tendency was significantly observed in subjects who ingested a small amount of soybean-derived ingredient. By ingesting *casei*, the risk of developing breast cancer tended to be further decreased (FIG. 2).

(v) These results were obtained by a conditional logistic regression analysis, in which only area of residence was used as a matching factor, and age was categorized into 40's and 50's and taken into consideration with a plurality of other adjustment factors. Moreover, an another analysis was carried out using the multiple models described in the above (ii) Analysis method for studying the relationship between ingestion of *Lactobacillus casei* and the development of breast cancer, and the robustness of the results was confirmed.

The invention claimed is:

1. A method for reducing the risk of developing breast cancer in a female subject at risk of developing breast cancer, the method comprising administering to the female subject a composition comprising living cells of *Lactobacillus casei* YIT 9029 (FERM BP-1366) before the development of breast cancer,
   wherein the female subject has an elevated risk of developing breast cancer, and wherein the elevated risk is determined by family history of the female subject.

2. The method of claim 1, wherein the composition is a food or drink comprising living cells of *Lactobacillus casei*.

3. The method of claim 1, wherein the composition is a fermented milk food or drink comprising living cells of *Lactobacillus casei*.

4. The method of claim 1, wherein the composition is administered 4 times per week.

5. The method of claim 1, wherein the composition is continuously administered for 10 or more years.

6. The method of claim 1, wherein the composition further comprises a soybean-derived ingredient.

7. The method of claim 4, wherein the composition is administered 4 times per week when the female subject is approximately 20 years old.

8. The method of claim 4, wherein the composition is administered 4 times per week after menopause.

* * * * *